United States Patent [19]

Labeeuw et al.

[11] Patent Number: 4,476,123

[45] Date of Patent: Oct. 9, 1984

[54] ANTIBIOTIC DERIVATIVES, DERIVED FROM CEPHALOSPORINS WITH THIAZOLYL SUBSTITUENTS, PHARMACEUTICAL PREPARATIONS AND SALTS THEREOF

[75] Inventors: Bernard Labeeuw, Montpellier; Ali Salhi, St Gely du Fesc, both of France

[73] Assignee: Sanofi, Paris, France

[21] Appl. No.: 353,890

[22] Filed: Mar. 2, 1982

[30] Foreign Application Priority Data

Mar. 3, 1981 [FR] France ................... 81 04243

[51] Int. Cl.$^3$ .................. A61K 31/545; C07D 501/56
[52] U.S. Cl. ...................................... 424/246; 544/22; 544/27
[58] Field of Search ............................ 544/27; 424/246

[56] References Cited

U.S. PATENT DOCUMENTS 4,237,128 12/1980 Cimarusti et al. ................. 544/27
4,399,131 8/1983 Durckheimer et al. ............ 424/246

Primary Examiner—Paul M. Coughlan, Jr.
Attorney, Agent, or Firm—Weingarten, Schurgin Gagnebin & Hayes

[57] ABSTRACT

The present invention relates to derivatives of the family of cephalosporins, of formula:

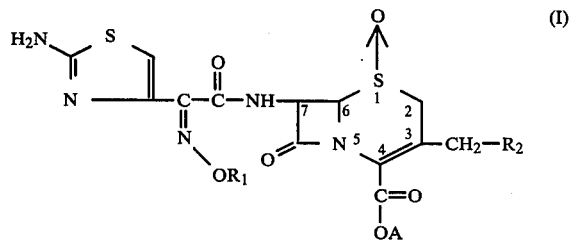

in which

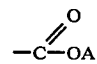

is an acid, a salt or an ester of this acid, $R_1$ is a group of form

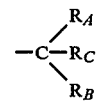

in which $R_A$ and $R_B$ are H or alkyl or form a saturated cyclobutyl or cyclopentyl ring and $R_C$ is H or COOH, $R_2$ is a thiazolium salt or a $OCOCH_2R_D$ group in which $R_D$ is a 1,3-thiazol-4-yl group.

The invention also relates to a process for preparing the products of formula (I) and to drugs containing said products.

7 Claims, No Drawings

ANTIBIOTIC DERIVATIVES, DERIVED FROM CEPHALOSPORINS WITH THIAZOLYL SUBSTITUENTS, PHARMACEUTICAL PREPARATIONS AND SALTS THEREOF

The present invention relates to derivatives of the family of cephalosporins, to a process for preparation thereof and to their application in therapeutics.

The compounds according to the invention respond to the following formula:

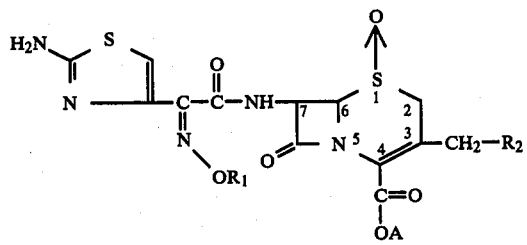

in which:
the group

in 4 position is an acid radical, or an alkaline or alkaline-earth metal salt or an amine salt, for example triethylamine or the ethanolamines, or an easily hydrolyzable or metabolically labile and pharmaceutically acceptable ester radical;

$R_1$ represents group

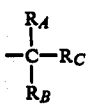

in which $R_A$ and $R_B$ each designate, independently, hydrogen or a lower alkyl group and preferably a methyl group, or, $R_A$ and $R_B$ taken together with the carbon atom to which they are attached, form a cyclobutyl or cyclopentyl ring and $R_C$ designates hydrogen or a carboxylic group;

$R_2$ designates a group

in which $R_D$ represents a 1,3-thiazol-4-yl cycle possibly substituted in 2 position by an amine group, or $R_2$ designates a thiazolium group with or without substitution in two position by an amino group.

Due to the presence in the formula of an oxime group, compounds (I) exist in two isomer forms: syn and anti. The syn isomers, of which the therapeutic activity is greater, are the preferred compounds.

It is understood that compounds (I) indicated hereinabove may exist:
either in the form indicated in formula (I)
or in tautomer form (I'):

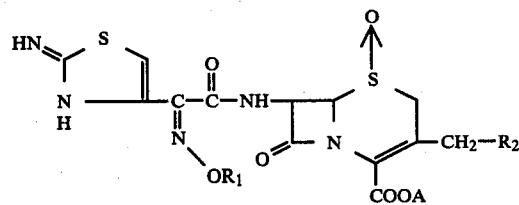

in which A, $R_1$ and $R_2$ have the meanings indicated hereinabove.

The invention also relates to a process for preparing the compounds of formula (I).

This process consists in firstly acylating 7-amino 3-bromo-methyl-3-cephem carboxylate of 4-tert butyl, 1-S-oxide (II) by the acid (III) according to the reaction diagram in which $R_1'$ is identical to $R_1$ or, when the latter comprises a carboxylic group, $R_1'$ represents the corresponding tert butyl ester.

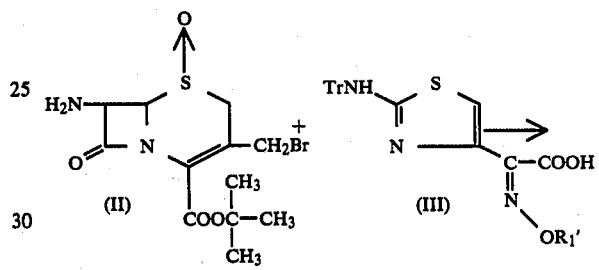

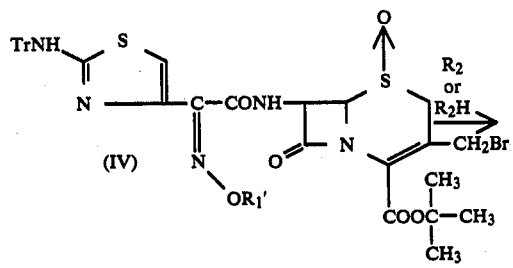

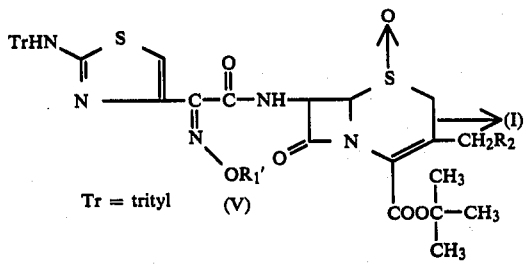

Tr = trityl (V)

Before carrying out the reaction of acylation, it is desirable to substitute the amino group of the acid by a protective group which is easy to eliminate later. Use may be made of the groups usually used in organic synthesis for the protection of the amino groups and in particular the trityl group.

Similarly, when the substituent $R_1$ of the acid (III) comprises a carboxylic group, it is necessary to convert the latter into ester. An ester is preferably chosen which is sufficiently labile to be able to regenerate the acid function at the end of reaction. The tert butyl ester is most often used.

To carry out the reaction of acylation, it is necessary to proceed with the activation of the carboxyl group of compound (III) preferably by conversion into anhydride with the aid of a carbodiimide, generally dicyclohexylcarbodiimide.

The reaction of activation is carried out within a suitable organic solvent such as tetrahydrofuran at a temperature of between 0° and 50° C. and preferably at ambient temperature. The reaction of activation is possibly facilitated by addition of a hydroxyl derivative such as 1-hydroxy benzotriazole.

The solution of the reagent of acylation thus obtained, from which the dicyclohexylurea formed is removed by filtration, is added to a solution of the compound (II) in a solvent such as dimethylformamide. The addition of the two reagents may also be effected in the reverse order.

By action on the compound (IV) thus obtained of an acid or an amine, the corresponding compound (V) is obtained. Operation is carried out in a suitable solvent such as dimethylformamide or N,N-dimethyl acetamide in the presence of a base such as triethylamine.

Finally, to arrive at compound (I), the protective group on the amine and the or each tert butyl ester group are eliminated by a known process, in particular by hydrolysis in an acid medium, using an organic acid such as formic acid or trifluoroacetic acid.

As far as the raw materials of the reaction are concerned, the compounds (II) and the compound (III) as well as its derivatives in which the amino group is blocked by a protective group, are known.

Compounds (I) of the invention in which A is other than H are obtained from the compounds (I) in which A is H by reactions known per se.

In this way, the mineral salts are obtained by action on the compounds (I) in which A is H of a mineral base such as sodium hydroxide or potassium hydroxide or bicarbonate of soda in equimolecular quantity; the reaction of salification is carried out in a solvent such as water or ethanol and the salt obtained is isolated by evaporation of the solution.

The salts of organic bases are obtained by action, on a solution of the acid (I, A=H) in a solvent or a mixture of suitable solvents, of an equimolecular quantity of the organic base. The salt is isolated by precipitation with ether.

The esters are obtained by the known processes of esterification; for example, the action of a halogen derivative on a salt such as the sodium salt of the acid will advantageously be used; the reaction will preferably be carried out in a solvent capable of dissolving the starting acid derivative for example in dimethylformamide.

The syn and anti isomers are obtained by suitably choosing the reagents.

The following examples will enable the scope of the invention to be more readily understood.

As is usual in this family of compounds, the products according to the invention have no distinct melting point but present only points of decomposition which do not characterize them.

The products will therefore be characterized by their nuclear magnetic resonance spectrum recorded at 60 MHz, the internal standard being hexamethyldisiloxane.

The spectra are recorded in deuterated dimethylsulfoxide.

The following abbreviations will be used:
S: singlet
D: doublet
D of D: doublet of doublet
e.S: enlarged singlet
M: multiplet
Q: quadruplet
AB: system AB
J: represents the coupling constant.

Moreover, elementary microanalyses were made in each case and are in agreements with the formulae indicated.

EXAMPLE 1

7[2(2-amino-4-thiazolyl)2-methoxyimino acetamide] 3-(4-thiazolyl acetoxymethyl)3-cephem 4-carboxylic acid, 1-S-oxide, syn isomer (I) $R_1=CH_3$; $R_2=$

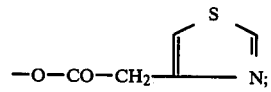

A=H (CM 40 579)

(a) 7-[2-(2-tritylamino 4-thiazolyl)2-methoxyimino acetamido] 3-bromomethyl 3-cephem carboxylate of 4 tert butyl, 1-S-oxide, syn isomer (IV) $R_1'=CH_3$ To a solution of 4.4 g of hydrochloride of 7-amino 3-bromomethyl 3-cephem carboxylate of 4-tert butyl, 1-S-oxide, in 70 ml of anhydrous methylene chloride, there are added, in a nitrogen atmosphere, 1.5 ml of triethylamine, 5.1 g of 2-(2-tritylamino 4-thiazolyl)2-methoxyimino acetic acid, syn isomer, 2.4 g of dicyclohexylcarbodiimide and 0.1 g of 1-hydroxy benzotriazole. Stirring is effected for 1 hour at ambient temperature then the dicyclohexylurea formed is filtered and the solution is concentrated to 20 ml in vacuo. The product is chromatographed over a column of silica gel (150 g). By elution with a 40-60 (vol/vol) hexane-ethyl acetate mixture, 4.8 g of the expected product are obtained after evaporation of the solvent.

NMR spectrum 1H at 8.82 ppm (NH-CO, D, J=8 Hz)-1H at 8.70 ppm (NH trityl, S)-15H at 7.32 ppm (H aromatics, S)-1H at 6.78 ppm (H thiazole, S)-1H at 5.79 ppm (H$_7$, D of D, J$_1$=8 Hz, J$_2$=4.5 Hz)-1H at 4.96 ppm (H$_6$, D, J=4.5 Hz)-2H at 4.50 ppm C$\underline{H_2}$Br, e.S)-3H at 3.78 ppm (NOC$\underline{H_3}$, S)-2H at 3.77 ppm ($\underline{CH_2}$S→O, e.S)-9H at 1.46 ppm

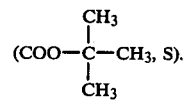

(b) 7-[2-(2-tritylamino 4-thiazolyl)2-methoxyimino acetamido] 3(4-thiazolyl acetoxymethyl)3-cephem carboxylate of 4-tert butyl, 1-S-oxide, syn isomer (V) $R_1'=CH_3$; $R_2=$

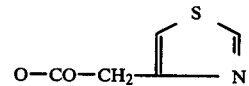

To a solution of 0.14 g of 4-thiazolyl acetic acid in 3.5 ml of N,N-dimethylacetamide are added 0.14 ml of triethylamine then 0.7 g of the brominated derivative obtained in paragraph (a).

The mixture is stirred for 20 hours at ambient temperature then 50 ml of ethyl acetate are added. The solution is washed with 20 ml of water then dried over magnesium sulfate. The solvent is evaporated to dryness in vacuo then the residue is taken up in 5 ml of chloroform and the solution is chromatographed over a column of silica gel (30 g). The product is eluted with a 10-90 (vol/vol) hexane-ethyl acetate mixture and 0.4 g of the expected product is obtained.

NMR spectrum: 1H at 9.05 ppm ($H_2$, thiazole in 3, D, J=2.5 Hz)-2H at 8.73 ppm (N$\underline{H}$ trityl, N$\underline{H}$-CO, M)-1H at 7.55 ppm ($H_5$, thiazole in 3, D, J=2.5 Hz)-15H at 7.26 ppm (H trityl, S)-1H at 6.80 ppm (H thiazole, S)-1H at 5.80 ppm ($H_7$, D, J=4 Hz)-1H at 5.15 ppm (C$\underline{H_2}$O CO-, A of AB, J=14 Hz)-1H at 4.90 ppm ($H_6$, D, J=4 Hz)-1H at 4.65 ppm (C$\underline{H_2}$O CO, B of AB, J=14 Hz)-7H at 3.73 ppm (C$\underline{H_3}$O N,

C$\underline{H_2}$S→O, M)-9H at 1.46 ppm

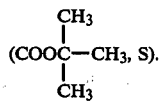

(c) CM 40 579

0.35 g of the compound obtained hereinabove is dissolved in 5 ml of trifluoroacetic acid and the solution is left at 23° C. for 30 minutes.

The solution is concentrated in vacuo up to 2 ml then 20 ml of ether are added. The precipitate is drained, washed with ether and dried in vacuo over phosphoric anhydride.

0.24 g of the expected product is obtained.

NMR spectrum: 1H at 9.0 ppm ($H_2$, thiazole in 3, S)-1H at 8.90 ppm (NH-CO, D, J=9 Hz)-3H at 8.4 ppm (N$\underline{H_2}$, COO$\underline{H}$, e.S)-1H at 7.52 ppm ($H_5$, thiazole in 3, S)-1H at 6.88 ppm (H thiazole, S)-1H at 5.87 ppm-($H_7$, D of D, $J_1$=9 Hz, $J_2$=4 Hz) 1H at 5.20 ppm (C$\underline{H_2}$O CO, A of AB, J=14 Hz)-1H at 4.96 ppm ($H_6$, D, J=4 Hz)-1H at 4.86 ppm (C$\underline{H_2}$O CO, B of AB, J=14 Hz)-7H between 3.5 and 4 ppm (C$\underline{H_3}$ON, C$\underline{H_2}$S→O, OCO C$\underline{H_2}$, M).

EXAMPLE 2

7-[2(2-amino 4-thiazolyl)2-carboxymethoxyimino acetamido] 3(4-thiazolyl acetoxymethyl)3-cephem 4-carboxylic acid, 1-S-oxide, syn isomer (I) $R_1$=$CH_2$COOH; $R_2$=

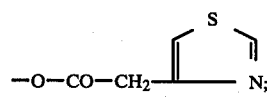

A=H (CM 40 517)

(a) 7-[(2-trítylamino 4-thiazolyl) t-butoxycarbonyl 2-methoxyimino acetamido] 3-bromomethyl 3-cephem carboxylate of 4-tert butyl 1-S-oxide, syn isomer

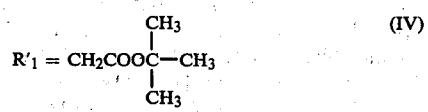

Operation is as in Example 1(a), replacing the 2-(2-tritylamino 4-thiazolyl) 2-methoxyimino acetic acid by an equivalent quantity of 2-(2-tritylamino 4-thiazolyl)t-butoxycarbonyl 2-methoxyimino acetic acid, syn isomer.

NMR spectrum: 1H at 8.75 ppm(N$\underline{H}$ trityl, S)-1H at 8.57 ppm (N$\underline{H}$CO, D, J=8.5 Hz)-15$\underline{H}$ at 7.28 ppm (H aromatics, S)-1H at 6.82 ppm (H thiazole, S)-1H at 5.84 ppm ($H_7$, D of D, $J_1$=8.5 Hz, $J_2$=4.5 Hz)-1H at 4.98 ppm ($H_6$, D, J=4.5 Hz)-4H at 4.50 ppm (—C$\underline{H_2}$Br and OC$\underline{H_2}$COO, S)-2H at 3.72 ppm (C$\underline{H_2}$S→O, e.S)-9H at 1.44 ppm

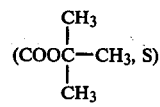

-9H at 1.35 ppm

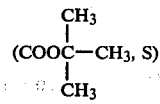

(b) 7[2-(2-tritylamino 4-thiazolyl)t-butoxycarbonyl 2-methoxyimino acetamido] 3-(4-thiazolyl acetoxymethyl)3-cephem carboxylate of 4-tert butyl 1-S-oxide, syn isomer

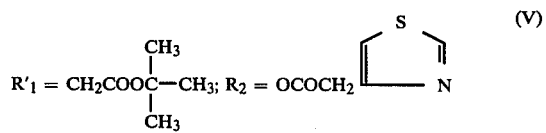

Operation is effected as in example 1(b) from the brominated derivative obtained hereinabove.

NMR spectrum: 1H at 8.65 ppm ($H_2$, thiazole in 3, D, J=2 Hz)-2H at 8.00 ppm (N$\underline{H}$CO, NH trityl, e.S.)-16H at 7.25 ppm ($H_5$, thiazole in 3, H trityl, S)-1H at 6.73 ppm (H thiazole, S)-1H at 5.96 ppm ($H_7$, M)-1H at 5.37 ppm (C$\underline{H_2}$OCO, A of AB, J=13 Hz)-1H at 4.70 ppm (C$\underline{H_2}$OCO, B of AB, J=13 Hz)-3H at 4.62 ppm ($H_6$, N-O-C$\underline{H_2}$-, e.S.)-2H at 3.85 ppm (OCOC$\underline{H_2}$, S)-1H at 3.70 ppm (C$\underline{H_2}$S→O, A of AB, J=17 Hz)-1H 3.32 ppm (C$\underline{H_2}$S→O, B of AB, J=17 Hz) 9H at 1.45 ppm

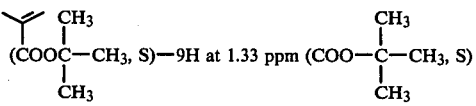

(c) CM 40 517

Operation is carried out as in Example 1(c) from the derivative obtained in the preceding paragraph.

NMR spectrum: 1H at 9.03 ppl ($H_2$, thiazole in 3, D, J=2.4 Hz)-1H at 8.73 ppm (NH CO, D, J=8.5 Hz)-1H at 7.53 ppm ($H_5$, thiazole in 3, D, J=2.4 Hz)-4H at 7.0 ppm (N$\underline{H_2}$, 2COO$\underline{H}$, e.S.)-1H at 6.82 ppm (H thiazole, 2)-1H at 5.82 ppm ($H_7$, D of D, $J_1$=8.5 Hz, $J_2$=4.5 Hz)-1H at 5.22 ppm (C$\underline{H_2}$O CO, A of AB, $J_{AB}$=14 Hz)-1H at 4.93 ppm ($H_6$, D, J=4.5 Hz)-3H at 4.60 ppm (O C$\underline{H_2}$COOH, S and C$\underline{H_2}$O CO, B of AB, J=14 Hz)-2H at 3.75 ppl (COC$\underline{H_2}$ thiazole, S)-2H at 3.68 ppm (C$\underline{H_2}$S→O, M).

EXAMPLES 3 TO 5

(a) Operation is carried out as in Example 1(a), replacing the 2-(2-tritylamino 4-thiazolyl) 2-methoxyimino acetic acid by an equivalent quantity of:

2-(2-tritylamino 4-thiazolyl) 2-(2-t-butoxycarbonyl 2-propyl oxyimino) acetic acid;

2-(tritylamino 4-thiazolyl) 2-(1-t-butoxycarbonyl 1-cyclobutyl oxyimino)acetic acid;

or 2-(tritylamino-4-thiazolyl) 2(1-t-butoxycarbonyl 1-cyclopentyl oxyimino) acetic acid.

By the same treatment, the compounds IV are respectively obtained, where:

$$-R'_1 = -\underset{\underset{CH_3}{|}}{\overset{\overset{CH_3}{|}}{C}}-COOtBu$$

NMR spectrum: 1H at 8.70 ppm (N$\underline{H}$-Trit, S)-1H at 8.07 ppm (N$\underline{H}$-CO, D, J=9 Hz)-15H at 7.25 ppm (H Trit, S)-1H at 6.72 ppm (H thiazole, S)-1H at 5.88 ppm (H$_7$, D of D, J$_1$=9 Hz, J$_2$=4 Hz)-1H at 4.96 ppm (H$_6$, D, J=4 Hz)-2H at 4.50 ppm (C$\underline{H}_2$Br, AB, J$_{AB}$=12 Hz)-2H at 3.77 ppm (C$\underline{H}_2$ in 2, e.S.)-9H at 1.45 ppm

-6H at 1.37 ppm

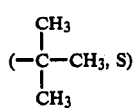

-9H at 1.27 ppm

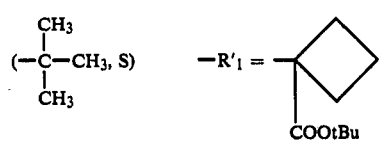

NMR spectrum: 1H at 7.90 ppm (N$\underline{H}$CO, D, J=9 Hz)-15H at 7.27 ppm (H aromatics, S)-1$\overline{H}$ at 6.97 ppm (N$\underline{H}$-trityl, e.S.)-1H at 6.65 ppm (H thiazole, S)-1H at 6.18 ppm (H$_7$, D of D, J$_1$=9 Hz, J$_2$=4.5 Hz)-2$\underline{H}$ at 3.4 ppm (C$\underline{H}_2$S→O, e.S.)-6H between 1.5 and 2.6 ppm (cyclobutyl, M)-9H at 1.46 ppm

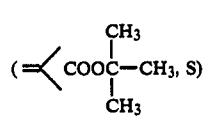

-9H at 1.36 ppm

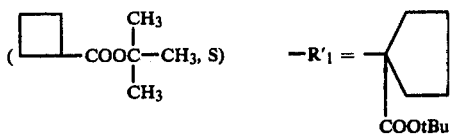

NMR spectrum: 1H at 7.83 ppm (N$\underline{H}$CO, D, J=9 Hz)-15H at 7.27 ppm (H aromatics, S)-1$\overline{H}$ at 6.93 ppm (N$\underline{H}$-trityl, e.S.)-1H at 6.14 ppm (H$_6$, D of D, J$_1$=9 Hz, J$_2$=4.5 Hz)-2H at 3.5 ppm (C$\underline{H}_2$S→O, AB, J$_{AB}$=17 Hz)-8H between 1.3 and 2.3 ppm (cyclopentyl, M)-9H at 1.50 ppm

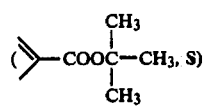

-9H at 1.35 ppm

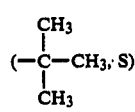

(b) By reacting on the brominated derivatives obtained hereinabove 4-thiazolyl acetic acid according to the technique of Example 1(b), then by proceeding with the unblocking of the amine and acid functions as indicated in Example 2(c), the following compounds (I) are obtained:

- CM 40 446

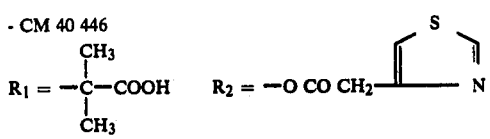

$$R_1 = -\underset{\underset{CH_3}{|}}{\overset{\overset{CH_3}{|}}{C}}-COOH \qquad R_2 = -O\,CO\,CH_2-\text{(thiazole)}$$

NMR spectrum: 1H at 9.0 ppm (H$_2$, thiazole in 3, e.S.)-6H at 8.5 ppm (NH$_2$, NHCO, 2COO$\underline{H}$, massive)-1H at 7.5 ppm (H$_5$, thiazole in $\overline{3}$, e.S.)-1H at $\overline{6}$.85 ppm (H thiazole, e.S.)-1H at 6.00 ppm (H$_7$, M)-1H at 5.27 ppm (CH$_2$OCO, A of AB, J$_{AB}$=13 Hz)-4H at 3.80 ppm (OCO C$\underline{H}_2$ and C$\underline{H}_2$S→O, M)-6H at 1.45 ppm

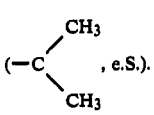

- CM 40 510

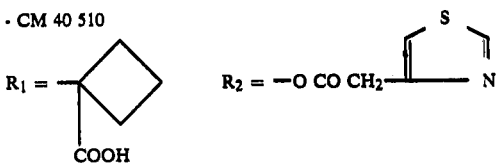

NMR spectrum: 1H at 8.95 ppm (H$_2$, thiazole in 3, e.S.)-1H at 8.55 ppm (N$\underline{H}$CO, D, J=9 Hz)-1H at 7.45 ppm (H$_5$, thiazole in 3, $\overline{e}$.S.)-4H at 7.25 ppm (H exchangeable, e.S.)-1H at 6.83 ppm (H thiazole, S)-1H at 5.96 ppm (H$_7$, D of D, J$_1$=9 Hz, J$_2$=4.5 Hz)-1H at 5.30 ppm (CH$_2$OCO, A of AB, J$_{AB}$=14 Hz) 1-H at 5.02 ppm (H$_6$, D, $\overline{J}$=4.5 Hz)-1H at 4.76 ppm (C$\underline{H}_2$ OCO, B of AB, J$_{AB}$=14 Hz)-2H at 3.82 ppm (O CO C$\underline{H}_2$, S) 2H at 3.70 ppm (CH₂S→O, e.S.)-6H between 1.5 and 2.6 ppm (cyclobutyl, M).

- CM 40 511

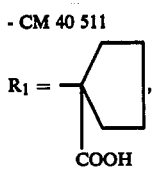 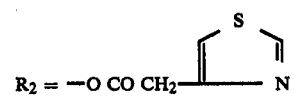

NMR spectrum: 1H at 9.0 ppm (H₅, thiazole in 3, e.S.)-1H at 8.46 ppm (NHCO, D, J=8.5 Hz)-1H at 7.50 ppm (H₂, thiazole in 3, e.S.)-5H at 7.30 ppm (H exchangeable, e.S.)-1H at 6.84 ppm (H thiazole, S)-1H at 6.00 ppm (H₇, D of D, J₁=8.5 Hz, J₂=4.5 Hz)-1H at 5.20 ppm (CH₂O CO, A of AB, J$_{AB}$=14 Hz)-1H at 5.00 ppm (H₆, D, J=4.5 Hz)-1H at 4.70 ppm (CH₂ O CO, B of AB, J$_{BA}$=14 Hz)-2H at 3.84 ppm (O CO CH₂, S)-2H at 3.75 ppm (CH₂S→O, e.S.)-8H between 1.3 and 2.4 ppm (cyclopentyl, M).

EXAMPLES 6 AND 7

7-[2-(2-amino 4-thiazolyl) 2-(1-carboxy 1-cyclobutyl-oxyimino) acetamido] 3-(2-amino-4-thiazolyl acetyloxymethyl) 3-cephem 4-carboxylic acid, 1-S-oxide, syn isomer (CM 40 681)

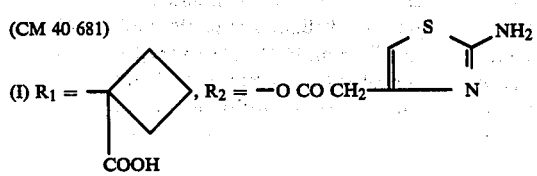

Operation is carried out as in Example 4, replacing in the second step, the 4-thiazolyl acetic acid by (2-tritylamino 4-thiazolyl) acetic acid in equivalent quantity.

After deprotection of the amine and acid functions, the expected compound CM 40 681 is obtained.

NMR spectrum: 6H between 8 and 11 ppm (2NH₂, 2COOH, e.S.)-1H at 8.60 ppm (NH CO, D, J=8.5 Hz)-1H at 6.80 ppm (H thiazole, S)-1H at 6.55 ppm (H thiazole in 3, S)-1H at 5.95 ppm (H₇, D of D, J₁=8.5 Hz, J₂=4 Hz)-1H at 5.20 ppm (CH₂ O CO, A of AB, J$_{AB}$=13 Hz)-1H at 4.95 ppm (H₆, D, J=4 Hz)-1H at 4.65 ppm (CH₂ O CO, B of AB, J=13 Hz)-4H at 3.62 ppm (CH₂S=O, O CO CH₂, M)-6H between 1.5 and 2.6 ppm (cyclobutyl, M).

Similarly, by operating as in Example 3 with (2-tritylamino 4-thiazolyl) acetic acid, the following compound I is obtained after deprotection:

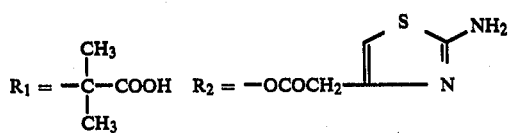

syn isomer (CM 40 733)

NMR spectrum: 6H between 7 and 10 ppm (2NH₂, 2COOH, M)-1H at 8.30 ppm (NH CO, D, J=9 Hz) 1H at 6.82 ppm (H thiazole, S)-1H at 6.42 ppm (H aminothiazole in 3, S)-1H at 6.00 ppm (H₇, D of D, J₁=9 Hz, J₂=4 Hz)-1H at 5.20 ppm (CH₂ O CO, A of AB, J$_{AB}$=13 Hz)-1H at 5.00 ppm (H₆, D, J=4 Hz)-1H at 4.70 ppm (CH₂ O CO, B of AB, J$_{AB}$=13 Hz)-4H at 3.65 ppm

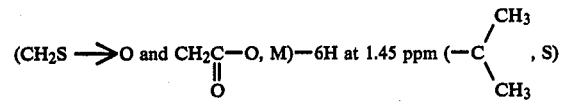

(CH₂S→O and CH₂C—O, M)—6H at 1.45 ppm

EXAMPLES 8 AND 9

Trifluoroacetate of 7-[2-(2-amino 4-thiazolyl) 2-(2-carboxy 2-propyl oxyimino) acetamido] thiazolium 3-methyl 3-cephem 4-carboxylic acid 1-S-oxide, syn isomer (CM 40 660)

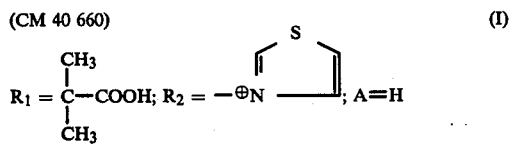

(a) Bromide of 7-[2-(2-tritylamino 4-thiazolyl) 2-(2-t-butoxycarbonyl 2-propyl 2-oxyimino) acetamido] thiazolium 3-methyl 3-cephem carboxylate of 4-t-butyl 1-S-oxide, syn isomer

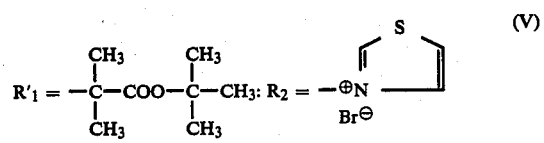

Stirring is effected for 24 hours at ambient temperature and away from light, of 1 g of the brominated derivative obtained in Example 3(a) and of 1.5 ml of thiazole. Ether is added and the precipitate is drained and washed with ether and dried in vacuo. 0.9 g of the expected product is obtained.

NMR spectrum: 1H at 10.1 ppm (H₂, thiazole in 3, e.S.)-1H at 8.65 ppm (NH-trityl, S)-2H at 8.32 ppm (H₄, and H₅, thiazole in 3, e.S.)-1H at 8.15 ppm (NHCO, D, J=8.5 Hz)-15H at 7.20 ppm (H aromatics, S)-1H at 6.70 ppm (H thiazole, S)-1H at 5.85 ppm (H₇ D of D, J₁=8.5 Hz, J₂=4 Hz)-2H at 5.40 ppm (CH₂N⊕, e.S.)

-1H at 5.15 ppm (H₆, D, J=4 Hz)-2H at 3.78 ppm (CH₂S→O, e.S.)-9H at 1.40 ppm

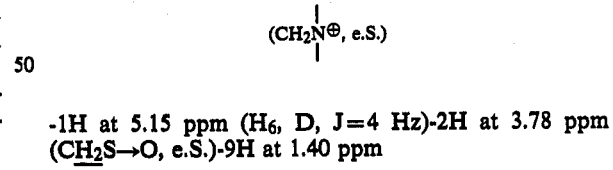

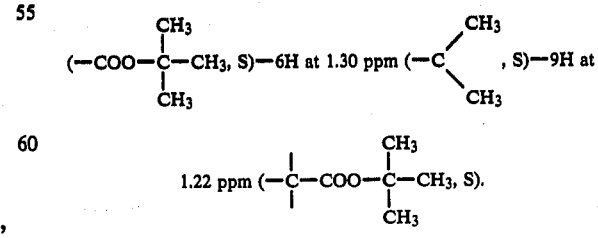

(b) CM 40 660
Operation is as in Example 1(c).
NMR spectrum: 1H at 10.1 ppm (H₂, thiazole in 3, e.S.)-3H at 8.35 ppm (NHCO, H₄, and H₅, thiazole in 3, e.S.)-1H at 6.77 ppm (H thiazole, S)-1H at 6.02 ppm (H₇, D of D, J₁=8.5 Hz, J₂=4 Hz)-2H at 5.40 ppm

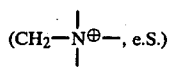

-1H at 5.0 ppm (H₆, D, J=4 Hz)-1H at 3.72 ppm CH₂S→O, A of AB, J$_{AB}$=17 Hz)-1H at 3.55 ppm (CH₂S→O, B of AB, J$_{AB}$=17 Hz)-6H at 1.42 ppm

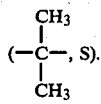

By replacing in step (a) the thiazole by 2-tritylamino thiazole, the following compound (I) is obtained in the same way, after deprotection:

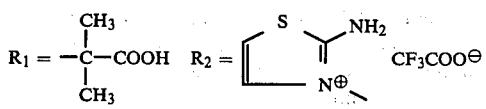

NMR spectrum: 2H at 9.80 ppm (NH₂ thiazolium)-1H at 8.50 ppm (NH CO, D, J=8.5 Hz)-2H at 7.80 ppm (NH₂, e.S.)-1H at 7.12 ppm (H₄ thiazole, D, J=4 Hz)-1H at 7.00 ppm (H₅ thiazole, D, J=4 Hz)-1H at 6.90 ppm (H thiazole, S)-1H at 6.01 ppm (H₇, M)-3H at 5.0 ppm (H₆ and CH₂N⁺, M)-2H at 3.70 ppm (CH₂S, AB, J$_{AB}$=17 Hz)-6H at 1.45 ppm

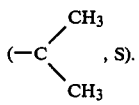

EXAMPLES 10 AND 11

By replacing in Example 8 the brominated derivative by the brominated derivatives obtained in Examples 4 and 5, the following compounds are obtained by the same process: (I)

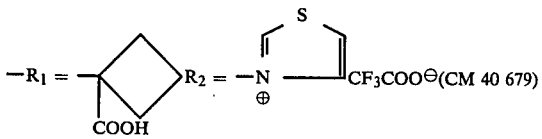

NMR spectrum: 1H at 10.1 ppm (H₂, thiazole in 3, S)-1H at 8.83 ppm (NHCO, D, J=8 Hz)-2H at 8.40 ppm (H₄, and H₅, thiazole in 3, S)-4H between 8.2 and 10 ppm (NH₂, 2COOH, e.S.)-1H at 6.82 ppm (H thiazole, S)-1H at 6.01 ppm (H₇, M)-2H at 5.45 ppm (CH₂⊕N≦, S)-1H at 5.03 ppm (H₆, D, J=4 Hz)-1H at 3.85 ppm (CH₂S→O, A of AB, J$_{AB}$=17 Hz)-1H at 3.57 ppm (CH₂S→O, B of AB, J$_{BA}$=17 Hz)-6H between 1.5 and 2.6 ppm (cyclobutyl, M).

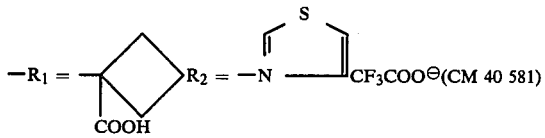

NMR spectrum: 1H at 10.2 ppm (H₂, thiazole in 3, S)-4H at 9.4 ppm (NH₂, 2COOH, e.S.)-3H at 8.45 ppm (NHCO, H₄, and H₅, thiazole in 3, M)-1H at 6.90 ppm (H thiazole, S)-1H at 6.10 ppm (H₇, D of D, J₁=9 Hz, J₂=4 Hz),-2H at 5.50 ppm (CH₂⊕N≦, S)-1H at 5.07 ppm (H₆, D, J=4 Hz)-1H 3.90 ppm (CH₂S→O, A of AB, J=17 Hz)-1H at 3.65 ppm (CH₂S→O, B of AB, J=17 Hz)-8H between 1.3 and 2.4 ppm (cyclopentyl, M).

The products of the invention have been studied as far as their pharmacological properties and more especially their bacteriostatic action are concerned.

In vitro bacteriostatic action was determined in a solid medium by the dilution method.

The results expressed in minimal inhibiting concentrations (CMI-μg/ml) relate to the results obtained on the strains of Pseudomonas A 22 IP and of Enterobacter P 99.

By way of comparison, the results obtained with a known product of relatively similar structure: 7-[2-(2-amino 4-thiazolyl) 2-methoxyimino acetamido] acetoxy 3-methyl 3-cephem 4-carboxylic acid 1-S-oxide, syn isomer (compound A) have been added to the Table.

| Strains | Minimal inhibiting concentrations in μg/ml Products | | | | | | | | |
|---|---|---|---|---|---|---|---|---|---|
| | CM 40581 | CM 40660 | CM 40679 | CM 40762 | CM 40446 | CM 40510 | CM 40681 | CM 40733 | Compound A |
| Pseudomonas A 22 IP | 8 | 4 | 4 | 8 | 32 | 16 | 8 | 8 | 256 |
| Enterobacter P99 | 8 | 4 | 4 | 16 | 8 | 4 | 4 | 8 | 64 |

These results show a particularly interesting activity of the products according to the invention on these strains which are usually not very sensitive to the antibiotics of the family of cephalosporins.

Furthermore, tests made on animals have shown no toxicity of the products according to the invention. The products of the invention may therefore be used as antibiotics in human or veterinary medicine. They may be used in all germ-sensitive bacterial infections.

The pharmaceutical compositions are made from compounds (I) in their acid form, or, when their solubility is insufficient, in the form of a salt.

The pharmaceutical compositions may be solid or liquid and may for example be in the form of tablets, capsules, granules, ointments, creams, gels or injectable preparations.

The dosage may vary in considerable proportions, in particular depending on the type and severity of the infection to be treated and depending on the mode of administration. In the adult and by the injectable route, it is most often between 0.250 g and 4 g per day.

By way of example of pharmaceutical composition, ampoules may be prepared, containing:

| | |
|---|---|
| CM 40 733 | 1 g |
| Bicarbonate of soda | 0.173 g |
| Water for injectable preparation | 4 ml |
| CM 40 679 | 1 g |
| Bicarbonate of soda | 0.156 g |
| Water for injectable preparation | 4 ml |

What is claimed is:

1. Derivatives of the family of cephalosporins having the formula:

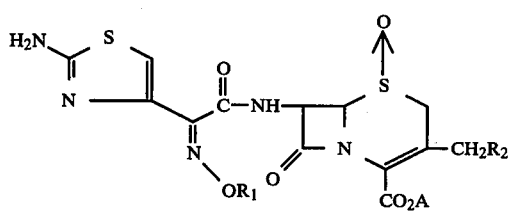

in which A is chosen from the group of cations consisting of alkali metal cations, alkaline earth cations, triethylammonium, 2-hydroxethylammonium, tertiary butyl, and hydrogen;

$R_1$ represents a

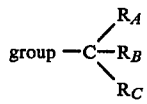

in which $R_A$ and $R_B$ each designate, independently, hydrogen or methyl, or $R_A$ and $R_B$ taken together with the carbon to which they are attached form a cyclobutyl or cyclopentyl ring, and $R_C$ is selected from the group consisting of hydrogen, carboxyl, and tertiarybutoxycarbonyl; and $R_2$ is selected from the group consisting of

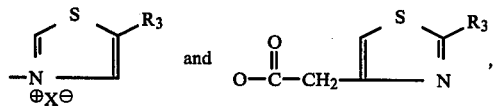

wherein $R_3$ is H or $NH_2$ and $X^-$ is a pharmaceutically-acceptable anion; or a pharmaceutically-acceptable acid addition salt of the compound in which A is a tertiary butyl or hydrogen and $R_C$ is tertiary butoxycarbonyl or carboxyl.

2. A derivative of claim 1, wherein the oximo group is in the syn isomeric form.

3. An antibiotic pharmaceutical composition useful in human and veterinary medicine, containing a therapeutically effective dose, as active ingredient, of a product according to claim 1 or 2.

4. An antibiotic pharmaceutical composition of claim 3, wherein the active ingredient is

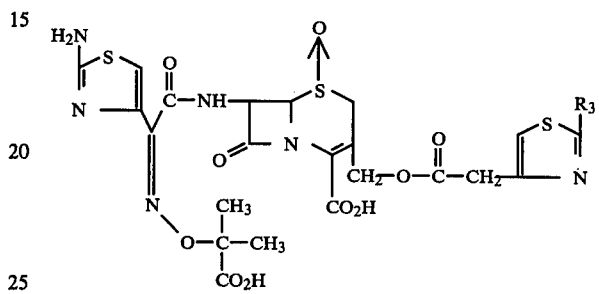

where $R_3$ is H or $NH_2$; or a pharmaceutically-acceptable acid addition salt thereof.

5. An antibiotic pharmaceutical composition of claim 3 wherein the active ingredient is

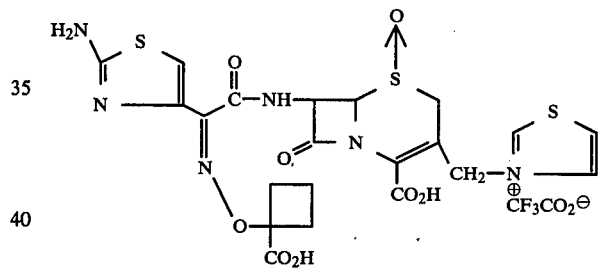

or a pharmaceutically-acceptable acid salt thereof.

6. A method of treating microbial infection in human and veterinary medicine, comprising administering a therapeutically-effective dose of a product according to claim 1 or 2.

7. A method of treating microbial infection in human and veterinary medicine, comprising admistering a therapeutically effective dose of a product according to claim 1 or 2 of between 0.250 g and 4 g per day.

* * * * *

UNITED STATES PATENT AND TRADEMARK OFFICE
CERTIFICATE OF CORRECTION

PATENT NO. : 4,476,123
DATED : October 9, 1984
INVENTOR(S) : Bernard Labeeuw, Ali Salhi It is certified that error appears in the above—identified patent and that said Letters Patent is hereby corrected as shown below:

Column 1  Line 36,   "$R_1$ represents group" should read --$R_1$ represents a group--

Column 4  Line 6,    "agreements" should read --agreement--

Line 39,   "NMR spectrum 1H" should read --NMR spectrum: 1H --

Column 9  Line 49,   "($CH_2 S = 0$," should read --($CH_2 S \rightarrow 0$,--

Column 13 Line 10,   "CM 40 679" should read --or CM 40 679--

Signed and Sealed this

Third Day of December 1985

[SEAL]

Attest:

DONALD J. QUIGG

Attesting Officer     *Commissioner of Patents and Trademarks*